(12) United States Patent
Xing

(10) Patent No.: US 6,697,452 B2
(45) Date of Patent: Feb. 24, 2004

(54) VERIFICATION METHOD OF MONITOR UNITS AND FLUENCE MAP IN INTENSITY MODULATED RADIATION THERAPY

(75) Inventor: Lei Xing, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 10/077,825

(22) Filed: Feb. 15, 2002

(65) Prior Publication Data

US 2003/0068009 A1 Apr. 10, 2003

Related U.S. Application Data

(60) Provisional application No. 60/269,684, filed on Feb. 16, 2001.

(51) Int. Cl.[7] .................................................. A61N 5/10
(52) U.S. Cl. ........................................ 378/69; 378/901
(58) Field of Search ............................ 378/64, 65, 901

(56) References Cited

U.S. PATENT DOCUMENTS

| | | | | |
|---|---|---|---|---|
| 6,260,005 B1 | * | 7/2001 | Yang et al. .................. | 703/11 |
| 6,504,899 B2 | * | 1/2003 | Pugachev et al. ............ | 378/65 |
| 6,560,311 B1 | * | 5/2003 | Shepard et al. .............. | 378/65 |

OTHER PUBLICATIONS

Georg D., and Dutreix A., 1999, "A Formalism to Calculate the Output Ratio in a Mini–Phantom for a GE Multileaf Collimator," Phys. Med. Biol., 42, pp. 521–536.
Boyer A.L., Xing L., Ma C., Curran B., Hill R., Kinia A., and Bleier A., 1999, "Theoretical Considerations of Monitor Unit Calculations for Intensity Modulated Beam Treatment Planning," Med. Phys., 26, pp. 187–195.
Geis P., Boyer A.L., "Use of a Multileaf Collimator as a Dynamic Missing–Tissue Compensator," Med. Phys. 23, pp. 1199–1205, 1996.
Kung J., Chen G., Kuchnir F., 2000, "A Monitor Unit Verification Calculation in Intensity Modulated Radiotherapy as a Dosimetry Quality Assurance," Med. Phys., 27, pp. 2226–2230.
G. J. Kutcher, et al., "Comprehensive QA for Radiation Oncology: Report of AAPM Radiation Therapy Committee Task Group 40," Medical Physics, 1994, 21(4), pp, 581–618.
L. Xing and J.G. Li, "Computer Verification of Fluence Maps in Intensity Modulated Radiation Therapy," Medical Physics, 2000, 27, pp. 2084–2092.
G.J. Kutcher, et al., "Comprehensive QA for Radiation Oncology: Report of AAPM Radiation Therapy Committee Task Group 40," Medical Physics, 1999, 21 (4): pp. 581–618.

* cited by examiner

*Primary Examiner*—David V. Bruce
(74) *Attorney, Agent, or Firm*—Lumen Intellectual Property Services, Inc.

(57) ABSTRACT

A general computer-implemented method and computer program for an independent MU or dose and fluence calculation of an intensity modulated photon field in intensity modulated radiation therapy (IMRT) is provided. The present invention provides for the verification MU or dose calculation in high dose regions or low dose regions. In general, the dose at an arbitrary spatial point is expressed as a summation of the contributions from all the beamlets in a treatment field, each modulated by a dynamic modulation factor. The verification of a low dose region is based on using the inverted field of the low dose region. The advantage of the present invention that it is an independent method and therefore generally applicable and useful irrespective of the type of leaf sequence algorithm and delivery machines. It provides an automated computer-implemented method or program that generalizes and simplifies dose verification in IMRT.

18 Claims, 10 Drawing Sheets

300

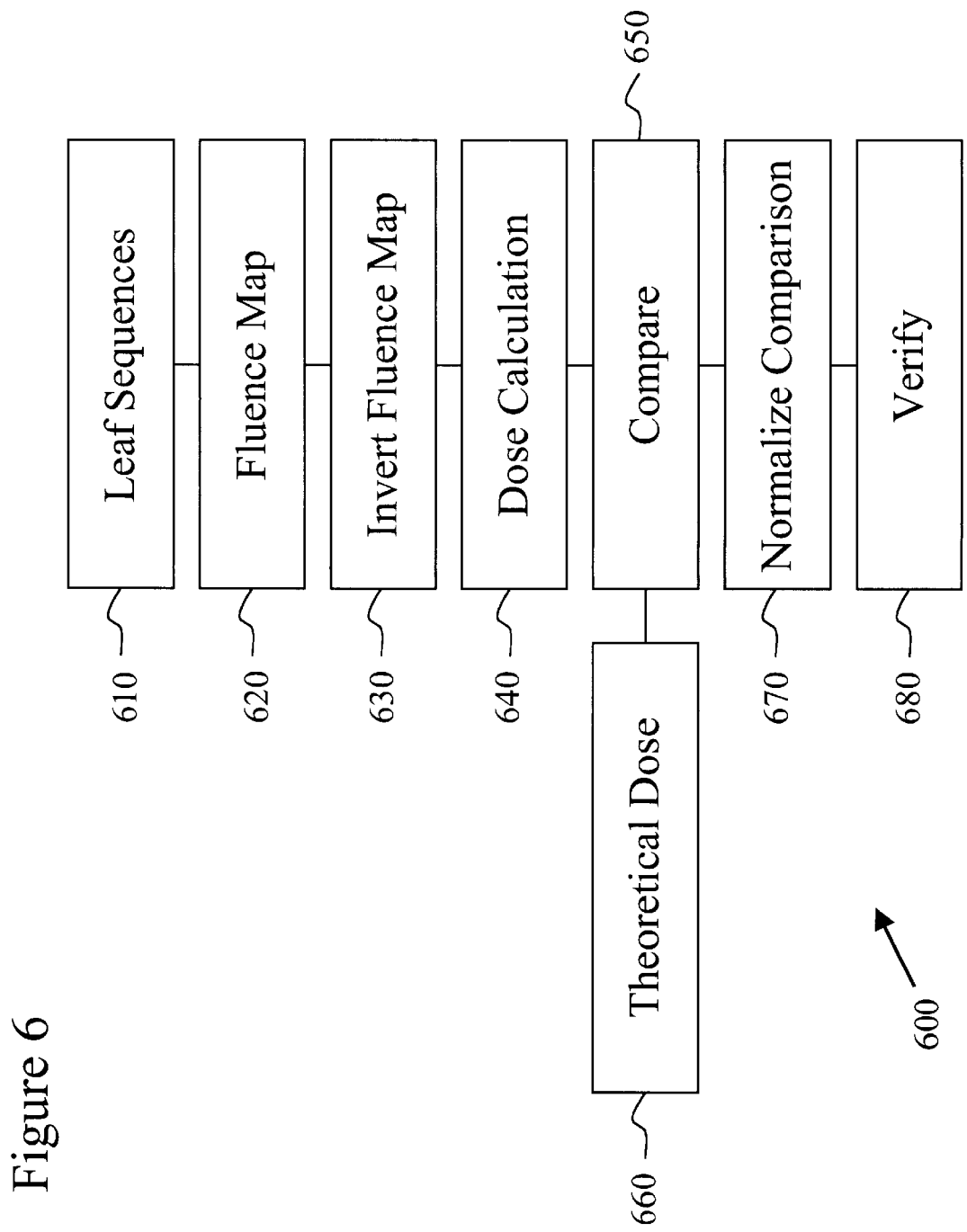

Figure 7a   Figure 7b   Figure 7c
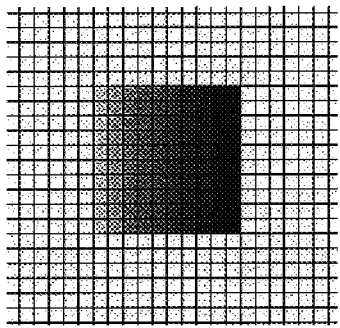 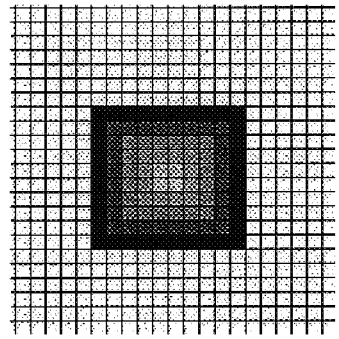 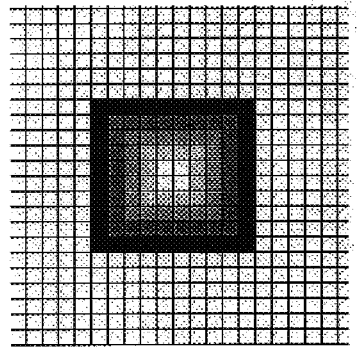
0%(White) - 100%(Black)

VERIFICATION METHOD OF MONITOR UNITS AND FLUENCE MAP IN INTENSITY MODULATED RADIATION THERAPY

CROSS-REFERENCE TO RELATED APPLICATIONS

This application is cross-referenced to and claims priority from U.S. Provisional Application No. 60/269,684 filed Feb. 16, 2001, which is hereby incorporated by reference.

FIELD OF THE INVENTION

The present invention relates generally to intensity modulated radiation therapy. More particularly, the present invention relates to a method for verification of monitor units and fluence map in intensity modulated radiation therapy.

BACKGROUND

Intensity modulated radiation therapy (IMRT) is a new modality of radiation therapy that shows promise for significantly improving dose conformation to the target and dose avoidance to the sensitive structures. IMRT has emerged from the developments of inverse planning and computer-controlled delivery using collimators (MiMiC) or multileaf collimators (MLC). An important problem in IMRT planning verification is how to efficiently verify the monitor unit (MU) calculation of an inverse planning system. An intensity modulated beam consists of a set of beamlets and is designed on a patient-specific basis. The beam can literally have any fluence profile and it is no longer possible to follow the manual MU check procedure of conventional conformal radiation therapy to validate an IMRT plan. Currently, the MU verification of IMRT is labor intensive, time consuming, costly and an institution dependent method.

One way to verify the MU or dose calculation of an IMRT treatment planning system is to sum the fractional MUs corresponding to the segmented fields. The MU calculation for a multileaf collimated static field has been described in the literature (Georg D and Dutreix A 1997. A formalism to calculate the output ratio in a mini-phantom for a GE multileaf collimator, *Phys. Med. Biol.* 42, 521–536). Boyer et al. (1999) have illustrated how MU settings are derived from the prescribed dose in CORVUS inverse planning system (NOMOS Corporation, Sewickley, Pa.) and experimentally verified the system using ionization chamber in a water phantom (Boyer A L, Xing L, Ma C, Curran B, Hill R, Kinia A and Bleier A 1999. Theoretical considerations of monitor unit calculations for intensity modulated beam treatment planning. *Med. Phys.* 26, 187–195). However, they did not touch the issue of how to use a computer to independently verify the MU settings provided by an inverse planning system. Geis and Boyer (Geis P and Boyer A L, Use of a multileaf collimator as a dynamic missing-tissue compensator, *Med. Phys.* 23, 1199–1205, 1996) investigated the feasibility of replacing conventional physical missing-tissue compensators by using dynamic multileaf collimators. Geis and Boyer (1996) introduced a method to calculate MU for dynamic compensated fields that is analogous to and expands upon methods used for conventional compensating filter MU calculation. The formula ignored the MLC leaf transmission and the MLC movements were designed to mimic a physical compensator. To obtain the MU of a dynamic compensator, it requires to know the MU setting of the corresponding physical compensator, which is generally not available and rendered the approach invalid for MU verification of an intensity modulated field. Kung and Chen (1999) have applied the Clarkson method to directly calculate the dose of an intensity modulated field at central axis and then compared the result with the result from the treatment planning system. (Kung J and Chen G 1999. A modified Clarkson integration (MCI) for IMRT. *Med. Phys.* 26: 1135; Kung J, Chen G Kuchnir F 2000, A monitor unit verification calculation in intensity modulated radiotherapy as a dosimetry quality assurance, *Med. Phys.* 27, 2226–2230). Their method has two major deficiencies. First, it did not separate the dosimetric effect of the dynamic modulation from the beamlet kernels and was thus applicable only when the Clarkson method was used for dose evaluation. It is practically impossible to generalize their approach for dose calculation based on other more advanced methods. The validity of the Clarkson-based approach becomes questionable as the spatial resolution of intensity modulation increases. The approach is also problematic for accelerators with variable jaw settings during IMRT delivery. Second, their approach fails to yield useful information when the verification point is located in a low dose region.

A key issue of quality assurance in IMRT is to establish a set of empirical criterions that are clinically acceptable and technically achievable. As far as the point dose is concerned, AAPM TG-40 recommends checking the point dose near the center of the tumor and a disparity should be resolved before commencing or continuing treatment if the difference is more than 5% [See for instance, G J Kutcher, et al., 1994 Comprehensive QA for radiation oncology: report of AAPM Radiation Therapy Committee Task Group 40. *Medical Physics*, 21(4): p. 581–618.]. Experience by the present inventor with IMRT dose validation in a high dose region indicates that dose agreement within 3%~5% is adequate and reflects the current standard practice. However, implementation of the criterion for all IMRT cases is complicated by the fact that the beam intensity is modulated and frequently the point of interest (POI) is located in the low dose region of one or more treatment fields. Generally, the uncertainty of dose calculation using simple techniques is higher in a low dose region due to the limited capability to model the MLC-modulated fluence and photon transport process in this situation. The relative dosimetric error can be as high as 5% to 40% in a low dose region when the data is normalized to the dose at the POI. In reality, a large relative error may rise from a true dosimetric error or simply because the point is in a low dose region which enhances the relative error.

Accordingly, there is a strong need to develop a general method for an independent MU or dose calculation of an intensity modulated photon field. Furthermore, there is a strong need to develop a method to verify high and low dose regions to provide better and unified quality assurance.

SUMMARY OF THE INVENTION

The present invention provides a general computer-implemented method and computer program for an independent MU or dose calculation of an intensity modulated photon field. The present invention provides a closed formula for point dose calculation in IMRT. Furthermore, the present invention provides a method to verify high or low dose regions in a treatment field. The dose at an arbitrary spatial point (either on the central axis or off-axis) is expressed as a summation of the contributions from all the beamlets, each is modulated by a dynamic modulation factor. Besides providing a clear physical picture, it allows one to implement the MU at different level of sophistication to meet the specific requirement of different system. Furthermore, the present invention provides a computer implemented method and computer program for the validation of MU setting when the verification point is in a low dose region using an inverted field approach. Finally, the present invention provides a computer implemented method and computer program for verifying a fluence map in a treatment field for intensity modulated radiation therapy.

It is the objective of the present invention to provide a calculation formalism for independent verification of the monitor units or point dose in either high or low dose regions in IMRT.

It is another objective of the present invention to provide a method of deriving the fluence map from the dynamic modulation factor distribution for independent fluence map calculation.

It is yet another objective of the present invention to verify or check both point dose and fluence map for the validation of an IMRT treatment plan.

The advantage of the present invention that is generally applicable and useful irrespective of the type of leaf sequence algorithm and delivery machines. The method of the present invention could also be applied for the MU verification of IMRT based on multivane intensity modulation collimators (MiMiC™) and other types of delivery systems (e.g. IMAT devices). The present invention is therefore institution independent. It provides an automated computer-implemented method or program that generalizes and simplifies dose verification in IMRT.

BRIEF DESCRIPTION OF THE FIGURES

The objectives and advantages of the present invention will be understood by reading the following detailed description in conjunction with the drawings, in which:

FIG. 6 shows method steps for the verification of a dose in a low dose region according to the present invention;

FIGS. 7a–c shows illustrative intensity maps according to the present invention;

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Figure 1:
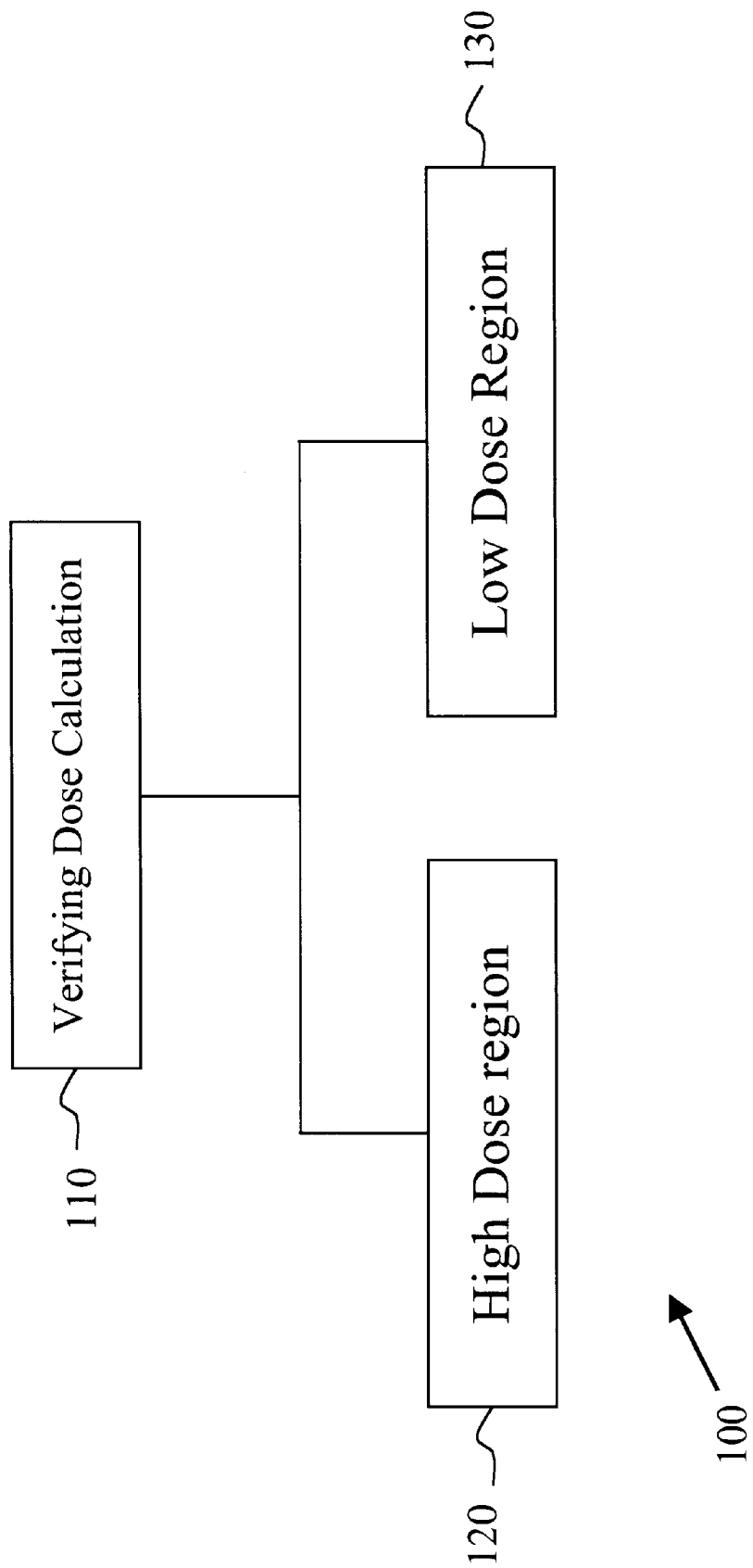
FIG. 1 shows the method of verifying a dose calculation for a high or low dose region according to the present invention.

The present invention provides an independent computer-implemented method for the verification of MU or dose calculation in IMRT. FIG. 1 shows the method 100 according to the present invention of verifying the dose calculation 110. This method includes a dose verification in the high dose region 120 or a dose verification in the low dose region 130. The following description will make clear the preferred method for verifying each region in a treatment field.

Figure 2:
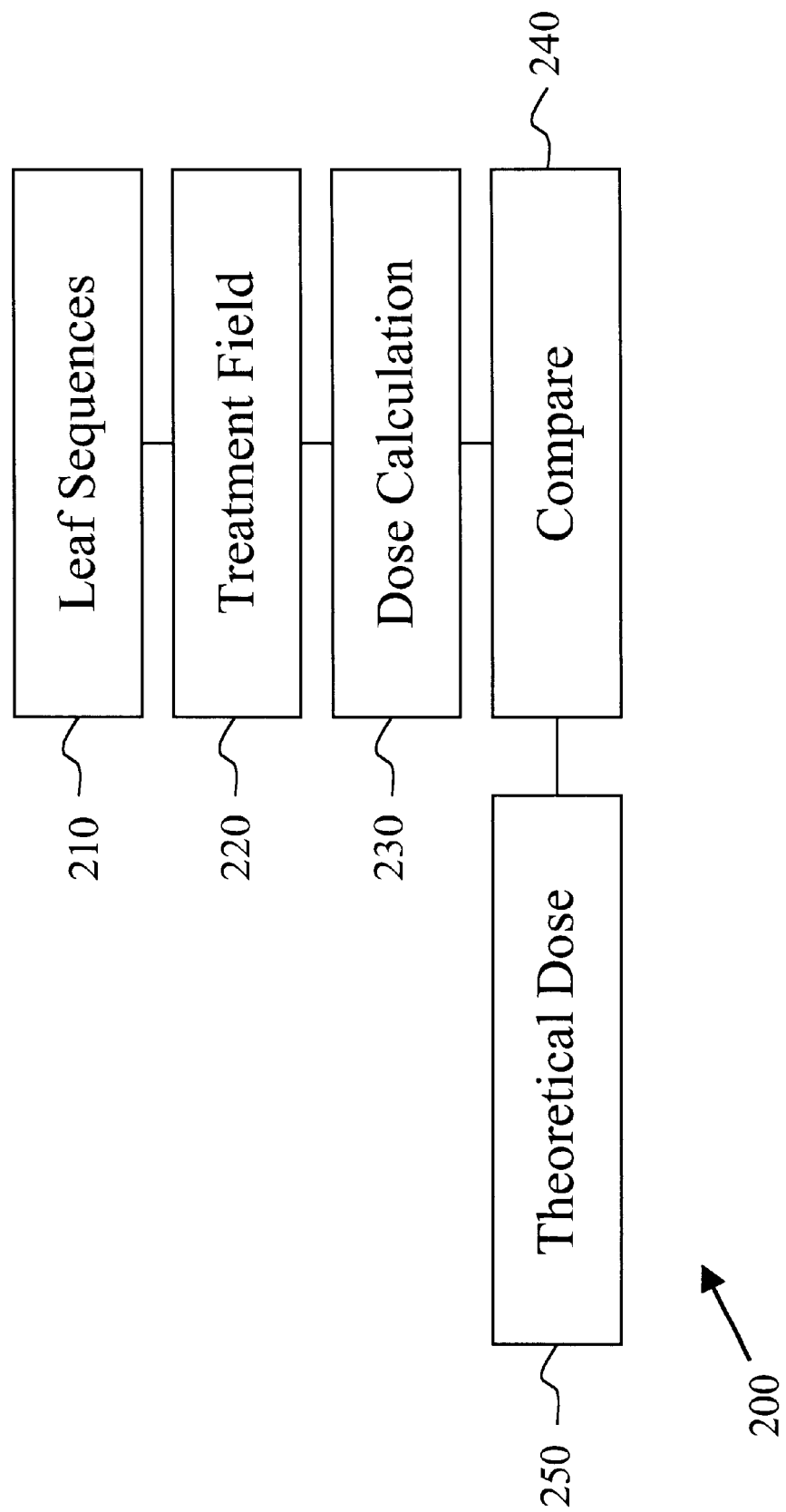
FIG. 2 shows method steps for an independent MU verification for a high or low dose region according to the present invention.

For a high or a low dose region, the computer-implemented method of independent MU verification 200 as shown in FIG. 2 entails providing multileaf collimator leaf sequences 210 for generating a treatment field 220 wherein the treatment field comprises M beamlets. The verification then entails the calculation of a dose 230 by a summation of all the contributions of M beamlets in the treatment field to which the dose pertains and wherein each of the M beamlets is modulated by a dynamic modulation factor. The calculated dose is compared 240 with a theoretical dose 250 predicted by a treatment planning system.

By way of illustration, let us first consider the case of a single incident beam. Multiple beams can be dealt with similarly as long as their relative weights are known. Assume that a treatment field defined by the jaws can be partitioned into M beamlets. Also, assume that there are K segments in the dynamic treatment field. The field shapes of these segments are known from the given leaf sequence file. The dose at a given point in the patient is a summation of the contributions of all segments of treatment, i.e., $$D = \sum_{k}^{K} MU_k d_k = MU \sum_{k}^{K} f_k d_k, \quad (1)$$

where $MU_k$ is the number of monitor units delivered by the $k^{th}$ segment, MU is the total monitor unit delivered by the beam, $f_k = MU_k/MU$ is the fractional MU of the $k^{th}$ segment, and $d_k$ is the dose per unit MU from the $k^{th}$ segment. Let $d^0_m$ be the dose contribution from the $m^{th}$ beamlet when it is open, and $d_m^t$ be the leakage dose per unit MU from the $m^{th}$ beamlet when it is blocked by the MLC. If we denote the set of beamlets inside the open field area of the $k^{th}$ beam segment by $A_k$, the dose from the $k^{th}$ segment per unit MU is given by:

$$d_k = \sum_{m \in A_k}^{M} d_m^0 + \sum_{m \notin A_k}^{M} d_m^t. \quad (2)$$

We introduce a notation:

$$\delta_{m,A_k} = \begin{cases} 1 & \text{if } m \in A_k \\ 0 & \text{if } m \notin A_k \end{cases}, \quad (3)$$

and further assume that the leakage dose can be related to the open beamlet dose by:

$$d_m^t = \alpha d_m^0,$$

where α is the transmission factor. Then, by exchanging the order of summations, we can recast Equation (1) as:

$$D = MU \sum_m^M C_m d_m^0, \quad (4)$$

where $$C_m = \sum_k^K [\delta_{m,A_k} + \alpha(1 - \delta_{m,A_k})] f_k. \quad (5)$$

Equation (4) relates to the dose at a given point to the setting of the monitor units MU. Equation (4) shows that, in order to obtain the dose of a multi-segment dynamic field, one only needs to perform the dose calculation of the contributing beamlets once. The increase in MUs required to deliver a modulated field is reflected by the $C_m$ factor defined by the summation in Equation (5). The summation represents the modulation of the dose at the point of interest taking into account the leaf leakage during the segments when the beamlets are blocked by the MLC. The calculation is facilitated by separating the open and blocked sets of beamlets, assuming that any beamlet is either completely open or blocked. Except for the beamlet size, which can be dependent of step size in a specific leaf sequence algorithm, the method of the present invention is independent of leaf sequence algorithms and delivery machines. All one needs for the calculation is the dose/MU and the transmission factor for each beamlet. The beamlet dose, $d_m^0$, can be calculated using a variety of methods, as simple as a Clarkson type of approach or as complex as Monte Carlo simulation.

To obtain the absolute value of MU using Equation (4), it is required to calculate the dose contributions from the beamlets. Given a collection of beamlets, there are many ways to calculate their dose contributions to a point. The method of the present invention proceeds by using the beamlets as the elementary building blocks. This decomposition seems to be more natural since it utilizes the field boundaries defined by the MLC. In the following we describe a simple way to carry out the MU calculation based on a modified Clarkson method (BIR (British Institute of Radiology) 1996. Central axis depth dose data for use in radiotherapy, British Journal of Radiology, Supplement No. 25, 1–183; Khan F 1994. *The physics of radiation therapy.* Baltimore: Williams & Wilkins).

The calculation point can be anywhere inside the field. As in the conventional treatment, it is convenient to choose the isocenter as the verification point because the source-to-skin distance (SSD) of the beam can be easily obtained and no off-axis ratio is involved. In this case, we consider the contribution from the central four beamlets as the "primary dose", denoted by $D_p$, and the contributions from the rest of the beamlets as "scatter". To be specific, let us assume that the beamlet size is 1 cm×1 cm. In reality each of the four beamlets in the central 2 cm×2 cm square can be either open or blocked. When all the four beamlets are open in the beam, the primary dose is given by:

$$D_p(cGy) = MU \times C_f(cGy/MU) \times S_c(l_{eq}) \times S_p(l=2 \text{ cm}) \times TMR(d, l=2 \text{ cm}) \quad (6)$$

where $C_f$ is the calibration factor of the linac, $S_c$ is the collimator scatter factor obtained by in-air measurement, $S_p$ is the phantom scatter factor defined as the ratio of the dose rate for a given field at reference depth to the dose rate at the same depth for the reference field size with the same collimator opening, $l_{eq}$ is the equivalent square of the field defined by the opening jaws, and TMR(d, l) is the tissue-to-maximum ratio for a square field of side l at the depth d.

The total scatter dose is calculated by summing up the contributions of all non-central beamlets. Each non-central beamlet acts as a scatter source and its contribution to the isocenter can be computed using the modified Clarkson method. To the first order approximation, the scatter contribution from a beamlet centered at a distance $r_m$ from the isocenter is given by $D_m = D_m'' a^2$. Here a is the beamlet size, and $D_m''$ is the scatter dose from a unit area at the center of the $m^{th}$ beamlet. To obtain $D_m''$, one may first compute the scatter dose from a circular ring with radius $r_m$ and then divide it by the area of the ring, $2 pr_m Dr_m$. To improve the accuracy, a beamlet can be further divided into a number of sub-beamlets and the dose from these sub-beamlets can be dealt in a similar manner as described above. A sum of the contributions of the corresponding sub-beamlets gives the scatter dose of the beamlet. We found that a sub-beamlet size of 0.5 cm×0.5 cm can yield satisfactory results consistent with experimental measurements for all clinical cases we have tested and further reduction in the sub-beamlet size does not give notable improvement. Of course, Equation (4) is quite general and allows one to use any other method for MU calculation based on the beamlet information.

The case of multiple incident beams can be dealt with similarly. One can proceed along two directions to verify the system calculation. One is to use the prescription information and fractional weighting of each beam to derive the monitor units for each beam. These MUs can then be compared with the system calculation. When the information of fractional weighting is not available (e.g., currently the Corvus system does not provide the relative weights of the incident beams), one can proceed to use $MU_j$ for each field provided by the treatment planning system to calculate the dose at a point using:

$$D = \sum_{j=1}^J D_j = \sum_{j=1}^J MU_j \left( \sum_{m=1}^{M_j} C_{m,j} d_{m,j}^0 \right), \quad (7)$$

where index j has been added to label each individual incident beam, and J is the total number of beams. The dose given by Equation (7) is then compared with that given by the treatment planning system. One should note that this method only verifies the composite dose, not that of individual beam.

Figure 3:
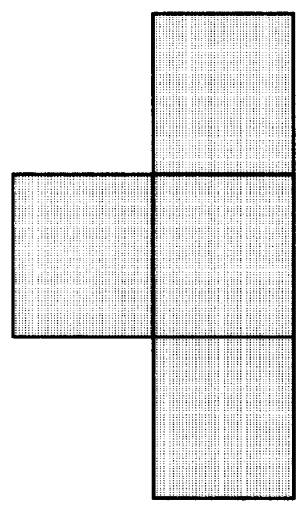
FIG. 3 shows an example of a delivery of a fluence profile according to the present invention.

FIG. 3 shows an example of a delivery of a simple fluence profile 300. There are several ways to generate the fluence map by segmented delivery as, for instance, shown by FIG. 4 and FIG. 5. In the delivery scheme shown in FIG. 4, the MLC leaf pair delivers the three fluence blocks in sequences. In this case, $f_1 = \frac{1}{4}, f_2 = \frac{1}{2}$, and $f_3 = \frac{1}{4}$. Substituting the $f_k$'s into Equation (4) and Equation (5) we have $$MU = \frac{4D}{(1 + 3\alpha)d_1^0 + (2 + 2\alpha)d_2^0 + (1 + 3\alpha)d_3^0}. \quad (8)$$

Figure 4:
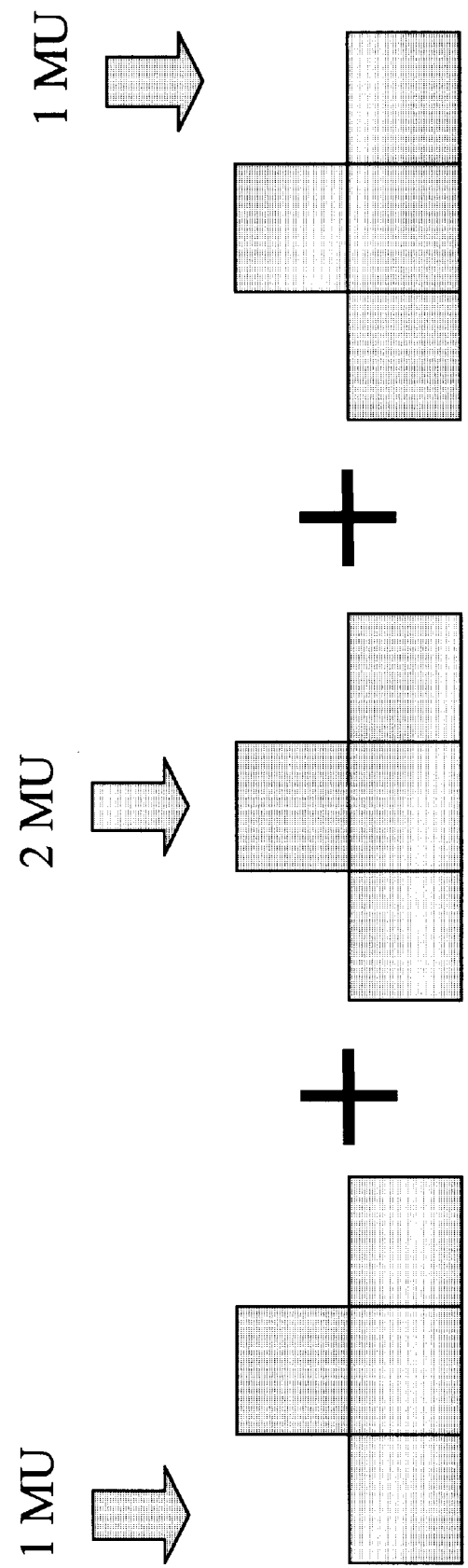
FIGS. 4–5 shows examples to generate a fluence map by segmented delivery according to the present invention.
Figure 5:
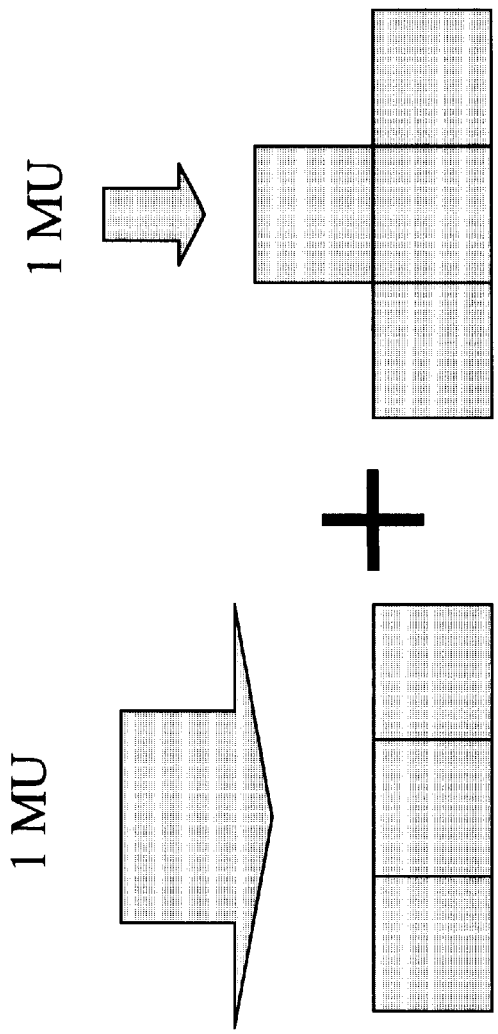

If we ignore the transmission dose, the above result indicates that in order to deliver a dose D to a point using the segmented delivery shown in FIG. 4, the delivery time is four times longer than that required by a delivery using a physical compensator. This agrees with an intuitive calculation based on the simple shape of the fluence map. For the delivery scheme shown in FIG. 5, it can be similarly shown that the delivery time is two times longer than that required by a physical compensator delivery if the leaf transmission is ignored. Note that the transmission doses in the two delivery schemes are different. The transmission is less if the delivery is more efficient.

The method of dose calculation works well for high dose regions in a treatment field. However, for a low dose region an additional verification is desirable. Therefore, the present invention further provides method steps 600 for the verification of a dose in a low dose region in a treatment field for intensity modulated radiation therapy as shown in FIG. 6. The method includes the step of providing a fluence map 620 of a treatment field which is generated based on provided multileaf collimator leaf sequences 610. An inverted map is determined 630 of the fluence map after which the dose of the inverted field is calculated 640. The calculated dose is compared with a theoretical dose 660 to determine 650 a dose difference. The dose difference is then normalized 670 by either a theoretical dose or the calculated dose. Eventually, the normalized dose is verified 680 with a criterion.

As an exemplary embodiment, the following description concentrates on IMRT based on a fixed-gantry delivery. As will be seen below, the method of the present invention can easily be generalized for fan beam IMRT. For convenience, we consider the case of a single incident beam and divide the beam into a grid of beamlets. The beamlet weights of an intensity-modulated field are usually normalized to the maximum beamlet. For delivery purpose, the beamlet weight is discretized into a finite number of levels (a typical value of intensity level in clinical IMRT is 10) with the maximum value of 100.

For each intensity modulated field (primal field), there exists a unique inverted field whose beamlet weights are defined as:

$$W_i(n) = W_{max} - W_p(n), \quad (9)$$

where $W_i(n)$ and $W_p(n)$ are the weights of the n-th beamlet in the inverted and primal fluence maps, respectively, and $W_{max}$ is the maximum beamlet weight of the primal beam. By convention we set the maximum beamlet weight of the primal field to be 100. The inverted field plus the primal field constitutes a uniform open field defined by setting the weights of all beamlets under the jaws to be 100. As a result of the inversion relation defined by Equation (9), the low dose region of the primal field corresponds to the high dose region of its inverted field, and vice versa. This complementary relation bridges what appears to be two independent schemes and allows one to validate the MU setting of the primal field by using the dosimetric data of the inverted field.

The complementary relation between the primal and inverted fields can be written explicitly as:

$$D_p + D_i = D_o, \quad (10)$$

where $D_p$, $D_i$ and $D_o$ are the doses of the primal, inverted and open fields, respectively. This relation provides an alternative way to compute the primal/inverted field dose using the information of the open field and the inverted/primal field. In practice, because the method does not directly invoke the forward calculation of the primary/inverted beam, the relation seems to be more suitable for an independent check of IMRT plans and provides assurance that would otherwise not be attainable with a direct calculation purely based on the primary/inverted fluence map.

The one-to-one correspondence between the primal and inverted fields provides a meaningful way to assess the dosimetric error of the primal field. Assuming that the open field dose can be computed or measured accurately, Equation (10) implies that clinically achievable dosimetric accuracy of the primal field depends on the dosimetric property of its inverted field, and vice versa. This indicates that, instead of directly evaluating the primal field, one can proceed by assessing the dose of the inverted field when the POI is located in a low dose region of the primal field. Because the POI is in the high dose region of the inverted field, the commonly used QA criterion (to be specific, one could assume that the tolerable relative dose error between the independent MU calculation and that of the treatment planning system is 4%) can be readily employed for QA decision-making.

Let us link mathematically the dosimetric errors of the primal and inverted fields. The relative dosimetric error of the inverted field is defined by:

$$r_i = [D_i^{TPS} - D_i]/D_i \quad (11)$$

where $D_i^{TPS}$ and $D_i$ are the inverted field dose from the treatment planning system and the independent calculation, respectively. Substituting Equation (10) into Equation (11) and assuming that the difference of the two open field doses obtained using the treatment planning system and the independent calculation is given by $DD_0 = D_0^{TPS} - D_0$, we have:

$$r_i = [D_p = D_p^{TPS} + \Delta D_0]/D_i = -(r_p - \Delta D_0/D_p)D_p/D_i \quad (12)$$

This equation reveals the "amplifying" effect of the low dose region on the relative error. For convenience, we assume that $DD_0 = 0$ since it is practically not difficult to achieve a higher degree of accuracy in open field dose calculation in both treatment planning system and the independent calculation system. In this case, if the maximum achievable relative dose error of the inverted field is 4%, the maximum achievable error of the primal field is given by 4% multiplied by the factor ($D_i/D_p$). Therefore, the complementary relation between the primal and the inverted fields allows us to use the QA criterion of the inverted field to estimate the dosimetric behavior of the primal field. As a result, a field would fail the QA test if the relative dose error of its inverted field were greater than 4% and a further QA action would be needed to make sure of the dosimetry of the system. Without the criterion based on the inverted field, it would be difficult to judge whether a QA action should be taken if we were to rely only on a relative dose error of the primal field dose.

There are two ways to calculate the dose of an intensity-modulated field in a low dose region. The first approach is to obtain directly the dose using the independent method for dose calculation as described according to Equations 4–5. An alternative way to calculate the dose of an intensity-modulated field in a low dose region is to use the complementary relation given in Equation (10). Based on the argument presented above, it can be seen that the dose of the inverted field offers a natural normalization for accessing the dosimetric accuracy of the original field. This has been stated implicitly from the standpoint of one-to-one correspondence between the primary and the inverted field doses. In practice, the validation in a low dose region could be done by the following steps (see also FIG. 6):

(i) Read in the MLC leaf sequence file of the primal field and compute its fluence map, $\{W_p(n)\}$.

(ii) Compute the fluence map of the inverted field $\{W_i(n)\}$ according to Equation (9).

(iii) Calculate the dose of the inverted field at the POI using the summation of contribution of all beamlets with each beamlet modulated by a dynamic modulation.

(iv) Compute the dose at the POI of the uniform rectangular field defined by the MLC leaves.

(v) Subtract the result of (iii) from that of (iv) to obtain the dose of the primal field.

(vi) Obtain the difference between the calculation result of (v) and that of the treatment planning system for the primary field.

(vii) Normalize the difference according to the inverted field dose obtained in step (ii).

(viii) Verify the normalized difference from (vii) with a criterion.

In step (i), it is required to compute the fluence map from an MLC leaf sequence file. This procedure has been described in some detail in Xing and Li (L Xing, and J G Li 2000, Computer verification of fluence maps in intensity modulated radiation therapy. *Medical Physics* 27: p. 2084–92) for both step-and-shoot and dynamic deliveries. After the leaf sequence file is read in, the movement of the MLC leaves is simulated and the fluence distribution at 100 cm source-surface distance (SSD) is computed by summing the contributions of each segment for a step-and-shoot delivery or of each time interval for a dynamic delivery. In a sense, this calculation procedure is to place an array of "virtual" detectors under the beam to "measure" the fluence distribution generated by the leaf sequence file. The choice of the fluence calculation model depends on the level of accuracy that one wishes to achieve. The present invention adapts a relatively simple fluence model, in which the fractional fluence per unit fractional MU is unity if the point of interest is exposed to radiation and a if it is blocked by an MLC leaf, where a is the transmission factor of MLC leaves.

In the above calculation, it is convenient to combine steps (i) and (iii) to compute the dose of the inverted field according to Equations 4–5. The dose of the inverted field is written as:

$$D = MU \sum_{m}^{M} (1 - C_m) d_m^0, \quad (13)$$

where $(1-C_m)$ is the dynamic modulation factor of the inverted field.

Figure 7D:
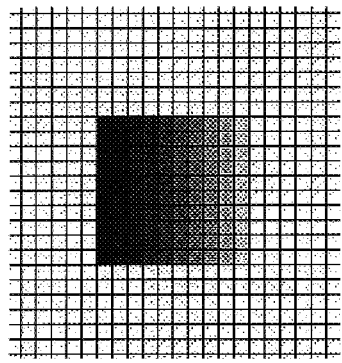
FIGS. 7d–f shows gray scale intensity maps of the inverted fields of FIGS. 7a–c respectively.
Figure 7E:
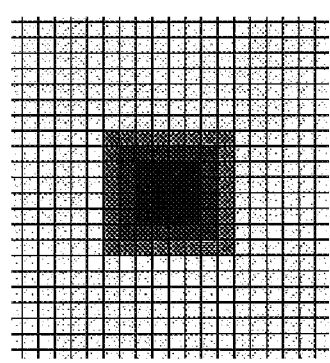
Figure 7F:
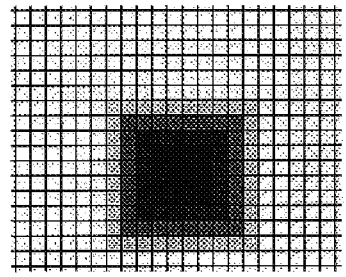
Figure 8A:
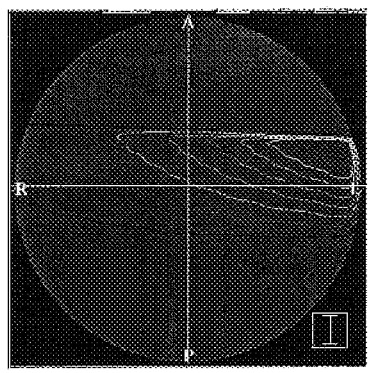
FIGS. 8a–c shows the isodose distributions on the central axial plane for the three 6 MV photon beams for the intensity maps in FIGS. 7a–c respectively.
Figure 8B:
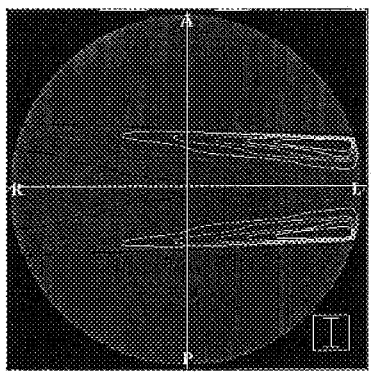
Figure 8C:
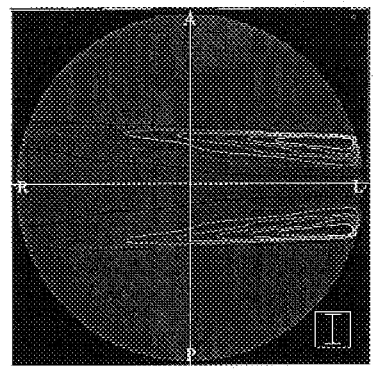

FIGS. 7a–c show illustrative intensity maps, consisting of a wedged field (FIG. 7a) and two well-shaped fields (FIGS. 7b–c) to illustrate the method of verifying a low dose region. The relative fluence distributions of the three fields are shown in FIGS. 7a–c in gray scale. The dose distributions of the three intensity modulated beams in a circular lucite phantom were computed using the CORVUS planning system (NOMOS Corporation, Sewickley, Pa.). FIGS. 8a–c show the isodose distributions on the central axial plane for the three 6 MV photon beams for the three intensity maps in FIGS. 7a–c respectively. The gray scale intensity maps of the inverted fields are shown in FIGS. 7d–f. In the three illustrations shown in FIGS. 7a–c, the sum of the primal and inverted fields constituted a 10×10 cm square field. Note that the open fields were defined by the MLC leaf settings instead of jaw settings (for a 10×10 cm field, our ion chamber measurement indicated that the isocenter dose of the MLC defined field was ~0.5% higher than that of the jaw defined field). The jaw transmission for Varian's accelerator (Varian Medical System, Palo Alto, Calif.) is less 0.5%. Typically, the jaws are set to a position of 0.2~0.8 cm larger than the rectangular MLC field defined by the IMRT field aperture and the scatter from the jaws is negligible. The wedged field represents an intuitive example and it is easy to conceive that, when the positive and negative wedges shown in FIG. 7a and FIG. 7d are combined, a uniform open field is the result. The two well-shaped fields are similar except that the central four beamlets are zero for the field shown in FIG. 7c. The isocenter is located in a low dose region in both cases. Once again, the sum of the primal and inverted field doses for the two cases was found to be equal to that of the open field dose to within 2.5% for both energies. For the third case shown in FIG. 7c, the isocenter dose is derived completely from scatter and transmission.

Figure 9:
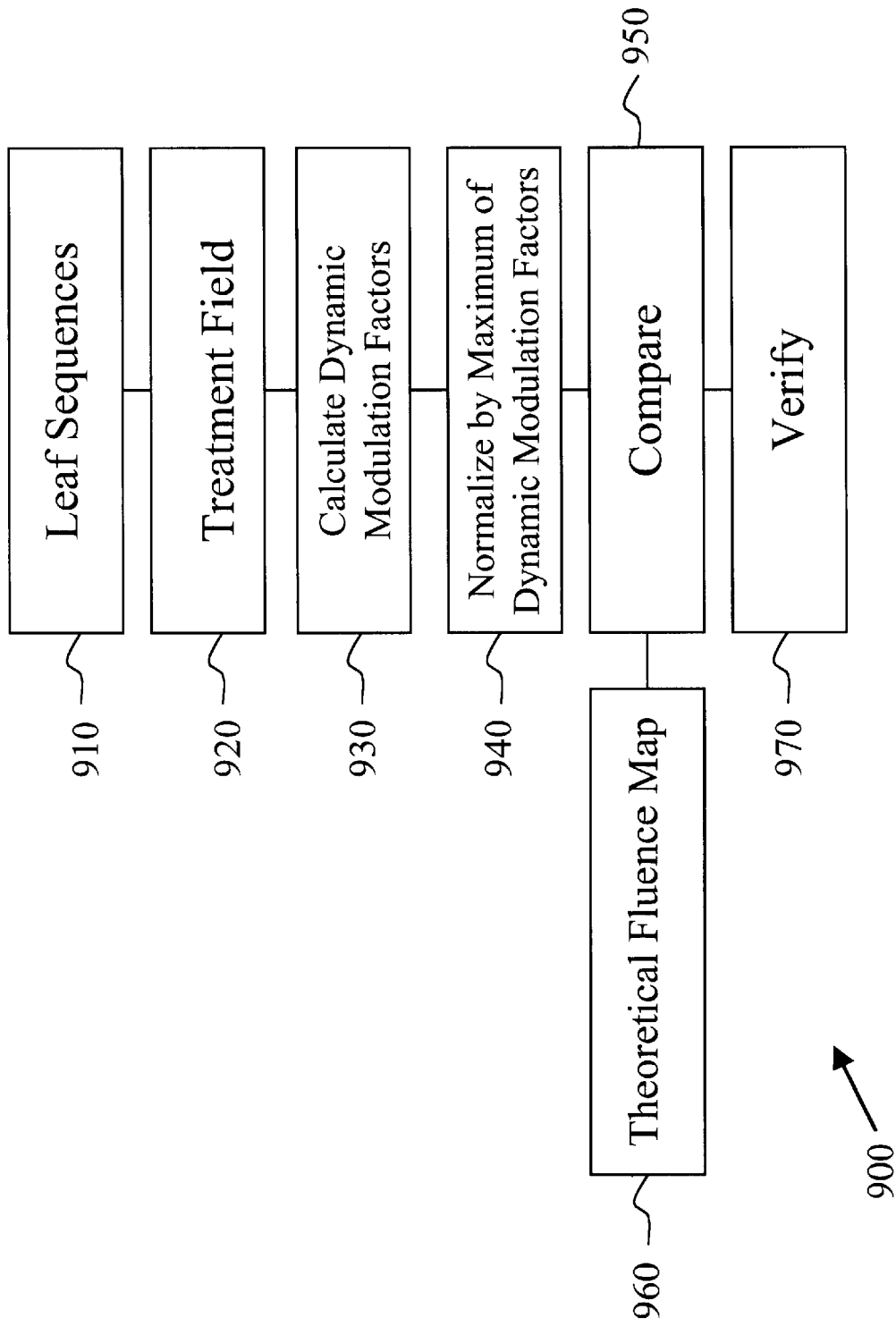
FIG. 9 shows method steps to verify the fluence map according to the present invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, the method of the present invention also includes the steps 900 to verify the fluence map generated by the leaf sequences 910 as shown in FIG. 9. As shown in FIG. 9, the verification of the fluence map includes the step of providing a treatment field 920 wherein the treatment field comprises M beamlets. For each beamlet, a dynamic modulation factor is calculated 930 after which the fluence map is calculated 940 by dividing each of the dynamic modulation factors by the maximum of all dynamic modulation factors. The calculated fluence map is then compared 950 with a theoretical fluence map 960. The comparison between the calculated 940 and theoretical fluence map 960 is then verified 970 for closeness using a criterion. Furthermore, the computer-implemented method of the present invention is not limited to any programming language or hardware platform. The present invention can also be used on a local computer or over a network. All such variations are considered to be within the scope and spirit of the present invention as defined by the following claims and their legal equivalents.

What is claimed is:

1. A computer-implemented method for an independent dose calculation in a treatment field in intensity modulated radiation therapy, comprising the step of verifying a dose region in said treatment field wherein said dose region is a high or a low dose region and wherein said verification of said low dose region is based on an inverted field of said low dose region.

2. The method as set forth in claim 1, further comprising the step of verifying a fluence map with a theoretical fluence map predicted by a treatment planning system.

3. The method as set forth in claim 1, wherein said dose verification is based on a summation of contributions of M beamlets in said treatment field and wherein each of said M beamlets is modulated by a dynamic modulation factor.

4. A program storage device accessible by a computer, tangibly embodying a program of instructions executable by said computer to perform method steps for an independent dose calculation in a treatment field in intensity modulated radiation therapy, said methods comprising the step of verifying a dose region in said treatment field wherein said dose region is a high or a low dose region and wherein said verification of said low dose region is based on an inverted field of said low dose region.

5. A computer-implemented method for an independent dose calculation in a treatment field in intensity modulated radiation therapy, comprising the steps of:

(a) providing multileaf collimator leaf sequences for generating said treatment field wherein said treatment field comprises M beamlets;

(b) calculating said dose by a summation of contributions of said M beamlets wherein each of said M beamlets is modulated by a dynamic modulation factor calculated for each of said M beamlets; and (c) comparing said calculated dose with a theoretical dose predicted by a treatment planning system.

6. The method as set forth in claim 5, wherein said calculation is according to $$D = MU \sum_{m}^{M} C_m d_m^0,$$

wherein D is said dose, MU is monitor units, $C_m$ is said dynamic modulation factor of said $m^{th}$ beamlet and $d^0_m$ is the dose of said $m^{th}$ beamlet.

7. The method as set forth in claim 5, wherein said dose calculation is of an inverted field of said treatment field.

8. The method as set forth in claim 5, wherein said treatment field comprises a low dose region.

9. The method as set forth in claim 5, further comprising the step of calculating a fluence map, wherein said fluence map is calculated by dividing each of said dynamic modulation factors by the maximum of all said dynamic modulation factors.

10. The method as set forth in claim 9, further comprising the step of comparing said calculated fluence map with a theoretical fluence map predicted by a treatment planning system and verifying said comparison with a criterion.

11. A program storage device accessible by a computer, tangibly embodying a program of instructions executable by said computer to perform method steps for an independent dose calculation in a treatment field in intensity modulated radiation therapy, said methods steps comprising:
   (a) providing multileaf collimator leaf sequences for generating said treatment field wherein said treatment field comprises M beamlets;
   (b) calculating said dose by a summation of contributions of said M beamlets wherein each of said M beamlets is modulated by a dynamic modulation factor calculated for each of said M beamlets; and
   (c) comparing said calculated dose with a theoretical dose predicted by a treatment planning system.

12. A computer-implemented method for verification of a dose in a low dose region in a treatment field in intensity modulated radiation therapy, comprising the steps of:
   (a) providing said multileaf collimator leaf sequences for generating said treatment field;
   (b) providing a fluence map of said treatment field;
   (c) determining an inverted field of said fluence map;
   (d) calculating said dose of said inverted field;
   (e) determining a dose difference between said calculated dose and a theoretical dose;
   (f) normalizing said dose difference with a theoretical dose or said calculated dose; and
   (g) verifying said normalized dose with a criterion.

13. The method as set forth in claim 12, wherein said dose calculation is a summation of contributions of M beamlets wherein each of said M beamlets is modulated by a dynamic modulation factor.

14. The method as set forth in claim 12, further comprising the step of verifying said fluence map.

15. A program storage device accessible by a computer, tangibly embodying a program of instructions executable by said computer to perform method steps for verification of a dose in a low dose region in a treatment field in intensity modulated radiation therapy, said methods steps comprising:
   (a) providing said multileaf collimator leaf sequences for generating said treatment field;
   (b) providing a fluence map of said treatment field;
   (c) determining an inverted field of said fluence map;
   (d) calculating said dose of said inverted field;
   (e) determining a dose difference between said calculated dose and a theoretical dose;
   (f) normalizing said dose difference with a theoretical dose or said calculated dose; and
   (g) verifying said normalized dose with a criterion.

16. A computer-implemented method for verifying a fluence map in a treatment field for intensity modulated radiation therapy, comprising the steps of:
   (a) providing said treatment field wherein said treatment field comprises M beamlets;
   (b) calculating a dynamic modulation factor for each of said M beamlets;
   (c) calculating said fluence map wherein said fluence map is calculated by dividing each of said dynamic modulation factors by the maximum of all said dynamic modulation factors; and
   (d) comparing said calculated fluence map with a theoretical fluence map, and verifying said comparison with a criterion.

17. The method as set forth in claim 16, wherein said fluence map comprises a low dose region.

18. A program storage device accessible by a computer, tangibly embodying a program of instructions executable by said computer to perform method steps of verifying a fluence map in a treatment field for intensity modulated radiation therapy, said methods steps comprising:
   (a) providing said treatment field wherein said treatment field comprises M beamlets;
   (b) calculating a dynamic modulation factor for each of said M beamlets;
   (c) calculating said fluence map wherein said fluence map is calculated by dividing each of said dynamic modulation factors by the maximum of all said dynamic modulation factors; and
   (d) comparing said calculated fluence map with a theoretical fluence map, and verifying said comparison with a criterion.

* * * * *